United States Patent
Chen et al.

(10) Patent No.: US 9,857,307 B2
(45) Date of Patent: Jan. 2, 2018

(54) ELEVATED SURFACE ENHANCED RAMAN SPECTROSCOPY RESONATOR STRUCTURES AND METHOD OF MAKING SAME

(71) Applicant: OPTOKEY, INC., Hayward, CA (US)

(72) Inventors: Fanqing Frank Chen, Moraga, CA (US); Robert P. Chebi, San Carlos, CA (US)

(73) Assignee: OPTOKEY, INC., Hayward, CA (US)

( * ) Notice: Subject to any disclaimer, the term of this patent is extended or adjusted under 35 U.S.C. 154(b) by 0 days.

(21) Appl. No.: 15/242,306

(22) Filed: Aug. 19, 2016

(65) Prior Publication Data

US 2017/0052121 A1    Feb. 23, 2017

Related U.S. Application Data

(60) Provisional application No. 62/207,778, filed on Aug. 20, 2015.

(51) Int. Cl.
  *G01N 21/55*    (2014.01)
  *G01N 21/65*    (2006.01)

(52) U.S. Cl.
  CPC ................... *G01N 21/658* (2013.01)

(58) Field of Classification Search
  CPC ............ G01N 21/658; G01N 21/554; G01N 2021/656; G01N 21/01; G01J 3/44; C12Q 2565/632; B82Y 20/00
  USPC ................ 356/445–448, 301, 244; 422/82.05–82.08; 436/164, 166, 169
  See application file for complete search history.

(56) References Cited

U.S. PATENT DOCUMENTS

| | | | |
|---|---|---|---|
| 8,269,963 B2 | 9/2012 | Ou et al. | |
| 8,685,743 B2 | 4/2014 | Zhang et al. | |
| 9,719,931 B2* | 8/2017 | Chen | G01N 21/658 |
| 2006/0273245 A1* | 12/2006 | Kim | G01J 3/0259 |
| | | | 250/226 |
| 2011/0109902 A1 | 5/2011 | Lin et al. | |
| 2012/0081703 A1 | 4/2012 | Moskovits et al. | |
| 2012/0136241 A1* | 5/2012 | Chen | A61K 49/0002 |
| | | | 600/420 |
| 2012/0208174 A1* | 8/2012 | Galush | G01N 33/54346 |
| | | | 435/5 |

(Continued)

FOREIGN PATENT DOCUMENTS

WO    2013 154770 A1    10/2013

OTHER PUBLICATIONS

Choi, et al., "Surface-enhanced Raman nanodomes," IOP Publishing., Nanotechnology, published on Sep. 13, 2010, pp. 1-7.

(Continued)

*Primary Examiner* — Hoa Pham
(74) *Attorney, Agent, or Firm* — DLA Piper LLP (US)

(57) ABSTRACT

In improved nonoplasmonic resonator (NPR) structure includes a silicon substrate having an upper surface, and a plurality of columns of silicon extending up from the substrate upper surface. Each of the columns includes a sidewall and terminates at an upper end. An insulation material is disposed on the sidewalls and upper ends of the columns. For each of the columns, the insulation material terminates in a bulge at an upper end of the column. A conductive layer is disposed on the insulation material along the column sidewalls and upper ends.

19 Claims, 4 Drawing Sheets

(56) References Cited

U.S. PATENT DOCUMENTS

| | | | |
|---|---|---|---|
| 2014/0224989 A1 | 8/2014 | Long et al. | |
| 2015/0223739 A1 | 8/2015 | Walavalkar et al. | |
| 2016/0049215 A1* | 2/2016 | Dionne | G21K 1/006 250/251 |

OTHER PUBLICATIONS

Hsieh, et al., "Enhanced Gold SERS Signals on HSR Surface Extrutions Generated on Carboxyl-Rich Polystyrene Beads," IEEE 2011, MEMS 2011, Cancun, MX dated Jan. 23-27, 2011, pp. 245-248.

Di, et al., "Inexpensive and Fast Fabrication of Ordered Gold Nanocone Arrays," 6$^{th}$ IEEE Intl. Conference of Nano/Micro Engineered and Molecular Systems, Kaohsiung, TW, dated Feb. 20-23, 2011, pp. 1-4.

Coppe., et al., "Metallic nanocone array photonic substrate for high-uniformity surface deposition and optical detection of small molecules," IOP Publishing, Nanotechnology 22, pp. 1-7, 2011.

Wu, et al., "Plasmonic Nanogap-Enhanced Raman Scattering Using a Resonant Nanodome Array," Wiley-VCH Verlag GmbH & Co. KGaA, Weinheim, 2012, Small 2012, pp. 1-8, wileyonlinelibrary.com.

* cited by examiner

ELEVATED SURFACE ENHANCED RAMAN SPECTROSCOPY RESONATOR STRUCTURES AND METHOD OF MAKING SAME

RELATED APPLICATIONS

This application claims the benefit of U.S. Provisional Application No. 62/207,778, filed Aug. 20, 2015, which is incorporated herein by reference.

FIELD OF THE INVENTION

The present invention relates to Surface Enhanced Roman Spectroscopy (SERS) for characterizing molecular properties, and more particularly to tunable nanoplasmonic resonators (NPRs) and methods of making NPRs.

BACKGROUND OF THE INVENTION

As shown in FIG. 1, it is presently known to use a nanoplasmonic resonators (NPR) 2 in the form of a thin dielectric layer 4 (e.g. $SiO_2$) sandwiched between two metallic nanodisks 6 on a quartz substrate 8 to enhance SERS (Surface Enhanced Raman Scattering) Raman intensity for the detection of protease and enzyme activity. The NPR 2 results in SERS hot-spots at desired locations and in small dimensions, allowing for multiplexed high-throughput detection and lab-on-chip applications. The resonance frequency of the NPR can be precisely tuned by varying the dielectric layer thickness and the aspect ratio of the NPR. Such NPR and SERS techniques are disclosed in U.S. Pat. No. 8,685,743, which is incorporated herein by reference for all purposes.

The NPR 2 results in SERS hot-spots at desired locations and in small dimensions, allowing for multiplexed high-throughput detection and lab-on-chip applications. The resonance frequency of the NPR can be precisely tuned by varying the dielectric layer thickness and the aspect ratio of the NPR. Such NPR and SERS techniques are known (see U.S. Pat. No. 8,685,743).

There is a need for improved techniques in forming NPRs, and there is a need for different NPR structures that further enhance the Raman intensity.

BRIEF SUMMARY OF THE INVENTION

In improved nonplasmonic resonator (NPR) structure includes a silicon substrate having an upper surface, a plurality of columns of silicon extending up from the substrate upper surface, each of the columns including a sidewall and terminating at an upper end, an insulation material disposed on the sidewalls and upper ends of the columns, wherein for each of the columns, the insulation material terminates in a bulge at an upper end of the column, and a conductive layer disposed on the insulation material along the column sidewalls and upper ends.

A method of forming nonoplasmonic resonator (NPR) structure includes providing a silicon substrate with an upper surface, forming a plurality of columns of silicon extending up from the substrate upper surface, each of the columns including a sidewall and terminating at an upper end, forming an insulation material on the sidewalls and upper ends of the columns, wherein for each of the columns, the insulation material terminates in a bulge at an upper end of the column, and forming a conductive layer on the insulation material along the column sidewalls and upper ends.

Other objects and features of the present invention will become apparent by a review of the specification, claims and appended figures.

BRIEF DESCRIPTION OF THE DRAWINGS

FIGS. 2A-4A are side cross sectional views showing the fabrication of an NPR structure according to a first embodiment.

FIGS. 2B-4B are top views showing the fabrication of the NPR structure according to the first embodiment.

DETAILED DESCRIPTION OF THE INVENTION

The present invention includes improved NPR structures and fabrication techniques that enhance hot spot formation and performance without having to utilize expensive and complex nano-meter scale lithography or techniques (i.e. E-Beam, iDuv, double patterning, etc.), and enable fabrication of structures with smaller dimensions, which are enabled by forming bulges elevated above a substrate surface as described below.

Figure 1:
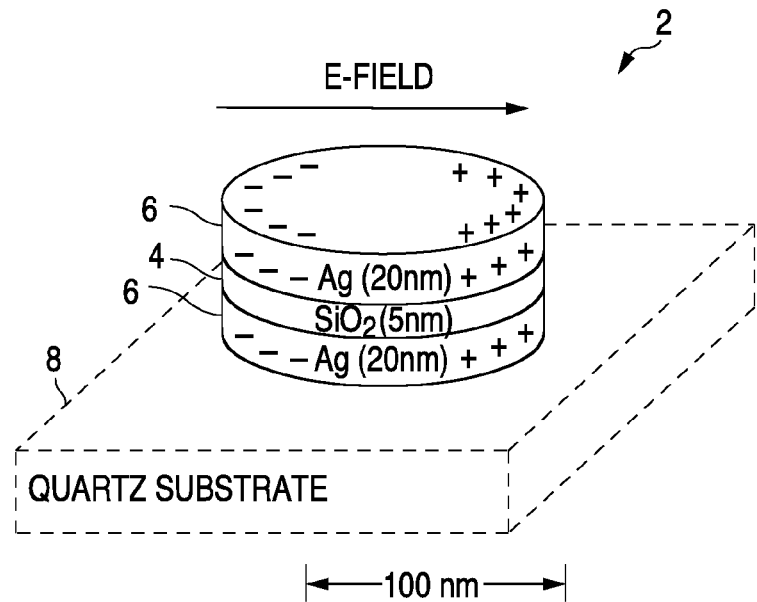
FIG. 1 is a perspective view of a prior art NPR structure.
Figure 2A:
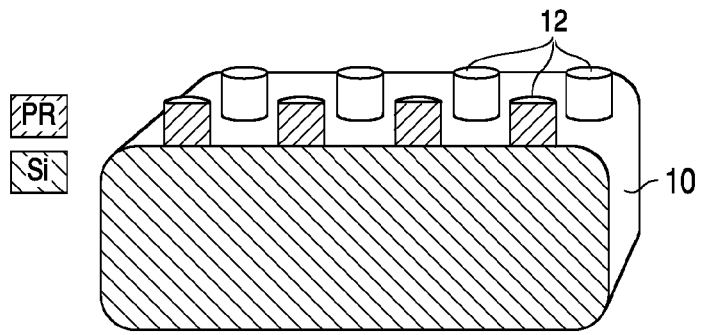
Figure 2B:
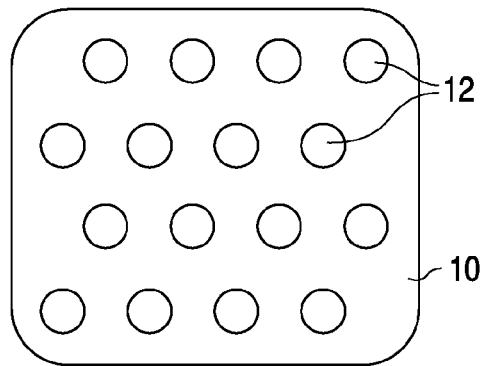

The fabrication of an elevated NPR structure begins with the flat silicon Si wafer substrate 10. Cylinders of photoresist PR 12 are formed on the wafer substrate 10, as shown in FIGS. 2A and 2B. Photo resist cylinders 12 are formed by depositing photo resist over the surface of the substrate 10, and patterning the photo resist using conventional photo-lithographic masking techniques by selectively exposing portions of the photo resist using a mask, followed by a photo resist etch, which removes some portions of the photo resist while leaving other portions of the photo resist intact. Each cylinder 12 can be round as shown, or oval. Each row of PR cylinders is preferably offset from the adjacent row in the column direction as shown.

Figure 3A:
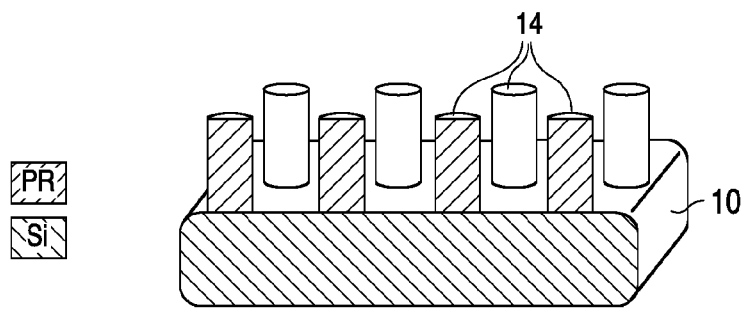
Figure 3B:
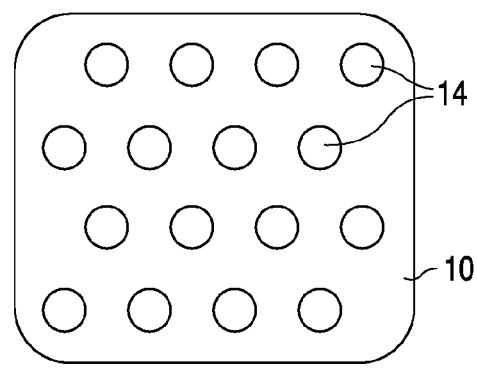

A silicon anisotropic etch is performed to remove exposed surface portions of substrate 10, leaving columns of silicon 14 underneath the cylinders of photoresist 12, as shown in FIGS. 3A and 3B (after photoresist removal). The silicon etch effectively lowers or recesses the upper surface of the substrate, or of that portion of the substrate, except for those portions thereof protected by the photo resist 12, resulting in columns of silicon 14 extending up from the now recessed upper surface of the silicon substrate.

Figure 4A:
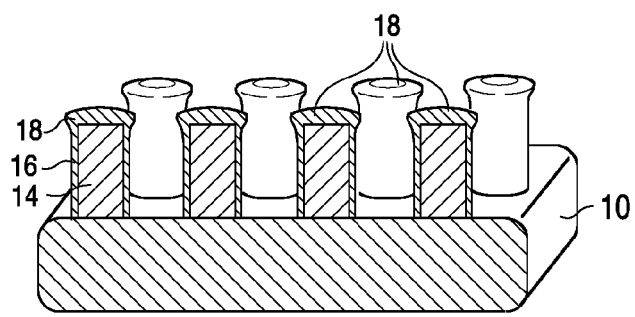
Figure 4B:
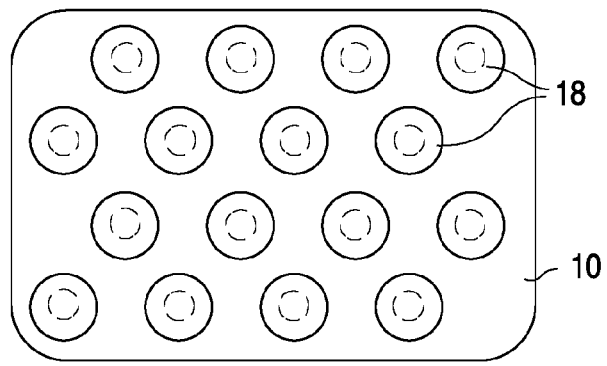

A layer of non-conformal LTO or PECVD silicon dioxide 16 is deposited on the structure in a manner that accentuates the "bread-loafing" phenomena, as shown in FIGS. 4A and 4B. The oxide 16 coats the sides of each of the silicon columns 14, and includes a bulge 18 at the top of the column 14 (i.e. a bulb or spherical shape of the oxide 16 at the top of the column 14 having a lateral dimension greater than the portions of the oxide 16 disposed along the sidewall of the column 14). Control of the oxide thickness and deposition parameters allow for achieving the desired shape and diameter of the bulge 18.

Figure 5:
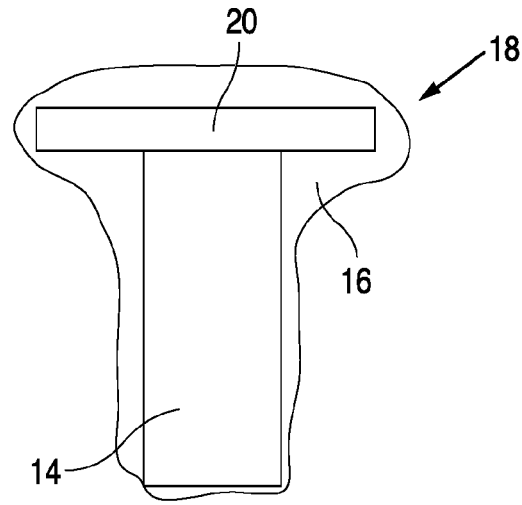
FIG. 5 is a side cross sectional view of an alternate embodiment for the NPR silicon column.

Alternately, the bulge 18 can be achieved by forming a hard mask layer over the silicon substrate 10 before photo resist cylinders 12 are formed (so that a disk 20 of the hard mask layer remains at the top of each silicon column 14 when columns 14 are formed). Then, an undercut silicon column etch is used to reduce the width of the silicon column 14 under each disk 20 (i.e. resulting in a T-Top formation). Silicon dioxide deposition and trim etch then follows to form the oxide 16 along the contour of the structure, and resulting in bulge 18, as shown in FIG. 5.

Figure 6A:
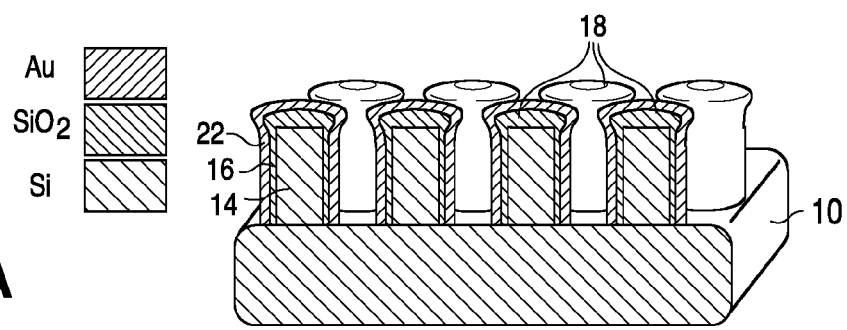
FIG. 6A is a side cross sectional view showing the completion of the fabrication of the NPR structure according to the first embodiment.
Figure 6B:
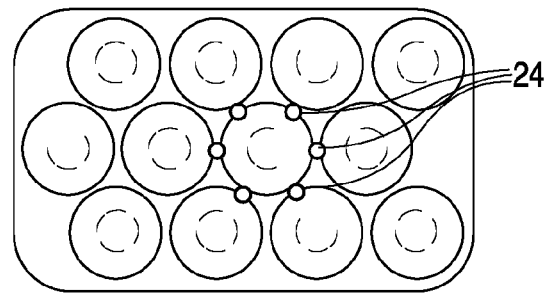
FIG. 6B is a top view showing the completion of the fabrication of the NPR structure according to the first embodiment.

A conformal layer of gold (Au) 22 is then formed on the structure, as shown in FIG. 6A. The thicknesses of the gold and silicon layers 22/16 can be optimized to produce the highest SERS amplification signal. The resulting structure is a plurality of the bulges 18 disposed in a plane above the substrate surface in an ordered array. Multiple points of the bulges 18 of adjacent columns 14 are preferably separated by only a few nanometers as shown in FIG. 6B. With the distance of these multiple points of gold layer 22 on adjacent bulges 18 being less than approximately 10 nanometers, the signal intensity from hot spots 24 there between increases significantly. In FIG. 6B, each bulge 18 is surrounded by six neighbors, thus producing 6 hot spots for each bulge 18.

Figure 7:
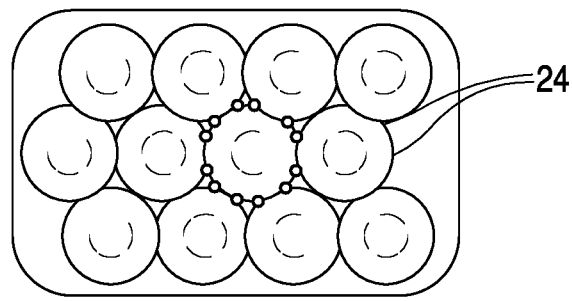
FIG. 7 is a top view showing an NPR structure according to a second embodiment.

FIG. 7 illustrates an alternate embodiment, in which the bulges 18 of adjacent columns 14 are touching bulges 18 of adjacent columns 14 (i.e. each bulge 18 is formed continuously with other bulges 18). Such a configuration would create a greater number of hot spots 24 (i.e. the number of hot spots 24 is doubled because there would be two hot spots 24 associated with each location in which the bulge 18 is touching another bulge).

Figure 8A:
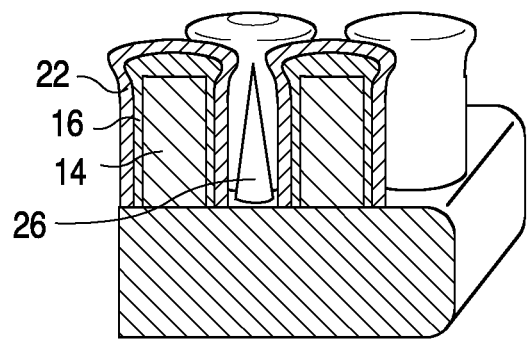
FIG. 8A is a side cross sectional view showing an NPR structure according to a third embodiment.
Figure 8B:
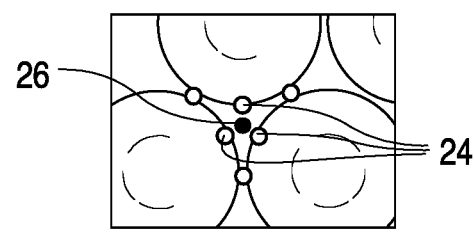
FIG. 8B is a top view showing the NPR structure according to the third embodiment.

FIGS. 8A and 8B illustrate another alternate embodiment, where gold covered spikes 26 extend up from the substrate surface and between columns 14, and terminate in a point proximate to the bulges 18. The spikes 26 are formed in a similar manner as the columns 14, but with decreasing size extending away from the substrate and no bulge at the top. Non-conformal oxide can be deposited simultaneously on the columns 14 and in spaces between the columns 14, where optimization of the spikes 26 can be accomplished in terms of aspect ratio, pitch and non-conformal oxide thickness. The spikes 26 are coated with gold in a similar manner as are the columns 14. With this configuration, each spike 26 can form additional hot spots 24, or hot spots that cover a range of adjacent surfaces of the spheres, in places where adjacent bulges cannot.

The elevated SERS structures can be fabricated very precisely, with high repeatability and surface periodicity, with sizes and separation tightly controlled by process conditions. The elevated SERS structures can be defined with I-Line or d-UV, as well as in nanometer scale using E-Beam Lithography. However, no advanced lithography is required to achieve very small gaps between adjacent bulges 18 and/or spikes 26. Finally, the pitch or periodicity of the structures may be optimized to contribute to constructive signal interference, thus maximizing the enhanced signal off the SERS structure surface.

It is to be understood that the present invention is not limited to the embodiment(s) described above and illustrated herein, but encompasses any and all variations falling within the scope of any claims. For example, references to the present invention herein are not intended to limit the scope of any claim or claim term, but instead merely make reference to one or more features that may be covered by one or more of the claims. Materials, processes and numerical examples described above are exemplary only, and should not be deemed to limit the claims. Specifically, silver could be used instead of gold for layer 22. The elevated SERS structures can have a thin nanometer layer of dielectric on top. While bulges are shown with spherical or bulb shapes, bulges 18 could be formed with other shapes, such as oval, square, rectangle, triangle, planar, or other regular or irregular shapes. While columns 14 are shown with a circular cross section, other cross sectional shapes could be used, including oval, square, rectangle, triangle, hexagon, star, etc. Square cross sectional shape has the advantage that there is a constant separation distance between columns. Further, as is apparent from the claims and specification, not all method steps need be performed in the exact order illustrated or claimed, but rather in any order that allows the proper formation of the elevated SERS structure of the present invention. Single layers of material could be formed as multiple layers of such or similar materials, and vice versa. Lastly, the terms "forming" and "formed" as used herein shall include material deposition, material growth, or any other technique in providing the material as disclosed or claimed.

It should be noted that, as used herein, the terms "over" and "on" both inclusively include "directly on" (no intermediate materials, elements or space disposed there between) and "indirectly on" (intermediate materials, elements or space disposed there between). Likewise, the term "adjacent" includes "directly adjacent" (no intermediate materials, elements or space disposed there between) and "indirectly adjacent" (intermediate materials, elements or space disposed there between), "mounted to" includes "directly mounted to" (no intermediate materials, elements or space disposed there between) and "indirectly mounted to" (intermediate materials, elements or spaced disposed there between), and "electrically coupled" includes "directly electrically coupled to" (no intermediate materials or elements there between that electrically connect the elements together) and "indirectly electrically coupled to" (intermediate materials or elements there between that electrically connect the elements together). For example, forming an element "over a substrate" can include forming the element directly on the substrate with no intermediate materials/ elements there between, as well as forming the element indirectly on the substrate with one or more intermediate materials/elements there between.

What is claimed is:

1. A nonplasmonic resonator (NPR) structure, comprising:
    a silicon substrate having an upper surface;
    a plurality of columns of silicon extending up from the substrate upper surface, each of the columns including a sidewall and terminating at an upper end;
    an insulation material disposed on the sidewalls and upper ends of the columns, wherein for each of the columns, the insulation material terminates in a bulge at an upper end of the column;
    a conductive layer disposed on the insulation material along the column sidewalls and upper ends.

2. The device of claim 1, wherein the conductive layer further extends along the substrate upper surface.

3. The device of claim 1, wherein the bulges are spaced apart from each other, and wherein at least two of the bulges are spaced apart from each other by no more than 10 nanometers.

4. The device of claim 1, wherein each of the bulges is touching at least one of the other bulges.

5. The device of claim 1, further comprising:
a plurality of disks, each disposed on one of the upper ends and within one of the bulges of the insulation material.

6. The device of claim 1, wherein the bulges are disposed in an ordered array in a plane above and separated from the substrate upper surface.

7. The device of claim 1, further comprising:
a plurality of spikes extending up from the substrate upper surface, wherein each of the spikes terminates in an upper end adjacent to and spaced apart from at least one of the bulges;
a conductive layer disposed on the spikes.

8. The device of claim 1, wherein each of the columns has a circular or oval cross section.

9. The device of claim 1, wherein each of the columns has a square or rectangular cross section.

10. A method of forming nonplasmonic resonator (NPR) structure, comprising:
providing a silicon substrate with an upper surface;
forming a plurality of columns of silicon extending up from the substrate upper surface, each of the columns including a sidewall and terminating at an upper end;
forming an insulation material on the sidewalls and upper ends of the columns, wherein for each of the columns, the insulation material terminates in a bulge at an upper end of the column;
forming a conductive layer on the insulation material along the column sidewalls and upper ends.

11. The method of claim 10, wherein the forming of the plurality of columns of silicon comprising:
forming photo resist on the substrate upper surface;
patterning the photo resist to selectively expose portions of the upper surface; and
etch the exposed portions of the upper surface.

12. The method of claim 10, wherein the forming of the conductive layer further comprises forming the conductive layer along the substrate upper surface.

13. The method of claim 10, wherein the bulges are spaced apart from each other, and wherein at least two of the bulges are spaced apart from each other by no more than 10 nanometers.

14. The method of claim 10, wherein each of the bulges is touching at least one of the other bulges.

15. The method of claim 10, further comprising:
forming a plurality of disks, each disposed on one of the upper ends;
wherein the forming of the insulation material includes forming the insulation around the disks such that each if the disks is disposed within one of the bulges of the insulation material.

16. The method of claim 10, wherein the bulges are disposed in an ordered array in a plane above and separated from the substrate upper surface.

17. The method of claim 10, further comprising:
forming a plurality of spikes extending up from the substrate upper surface, wherein each of the spikes terminates in an upper end adjacent to but spaced apart from at least one of the bulges;
forming a conductive layer on the spikes.

18. The method of claim 10, wherein each of the columns has a circular or oval cross section.

19. The method of claim 10, wherein each of the columns has a square or rectangular cross section.

* * * * *